United States Patent
Asada et al.

(10) Patent No.: US 8,143,312 B2
(45) Date of Patent: Mar. 27, 2012

(54) TRANSPARENT EYE DROPS CONTAINING LATANOPROST

(75) Inventors: Hiroyuki Asada, Osaka (JP); Akio Kimura, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 5 days.

(21) Appl. No.: 10/526,822

(22) PCT Filed: Sep. 8, 2003

(86) PCT No.: PCT/JP03/11402
§ 371 (c)(1),
(2), (4) Date: Mar. 4, 2005

(87) PCT Pub. No.: WO2004/022063
PCT Pub. Date: Mar. 18, 2004

(65) Prior Publication Data
US 2006/0069162 A1    Mar. 30, 2006

(30) Foreign Application Priority Data

Sep. 9, 2002 (JP) ................................. 2002-263030
Sep. 9, 2002 (JP) ................................. 2002-263035
Sep. 9, 2002 (JP) ................................. 2002-263039

(51) Int. Cl.
*A61K 31/19* (2006.01)
(52) U.S. Cl. ....................................... 514/573; 514/912
(58) Field of Classification Search .................. 514/573, 514/912
See application file for complete search history.

(56) References Cited

U.S. PATENT DOCUMENTS

| | | | | |
|---|---|---|---|---|
| 6,166,073 A | * | 12/2000 | Dean et al. ..................... | 514/530 |
| 2002/0103255 A1 | | 8/2002 | Hellberg et al. | |

FOREIGN PATENT DOCUMENTS

| | | |
|---|---|---|
| EP | 0 603 800 A1 | 6/1994 |
| EP | 0850926 A2 | 7/1998 |
| JP | 46-26986 B | 8/1971 |
| JP | 62-277323 A | 12/1987 |
| JP | 1-246227 A | 10/1989 |
| JP | 2721414 B2 | 11/1997 |
| JP | 2003-292442 A | 10/2003 |
| WO | WO 90/02553 A1 | 3/1990 |
| WO | WO 97/23225 A1 | 7/1997 |
| WO | WO 98/53809 A1 | 12/1998 |
| WO | WO 00/04898 A1 | 2/2000 |

OTHER PUBLICATIONS

Copending, related U.S. Appl. No. 10/524,996 (pp. 1-18; 2 sheets drawings; and Declaration and Power of Attorney).
Supplementary European Search Report date May 26, 2010 for EP 03794272.

* cited by examiner

*Primary Examiner* — Zohreh Fay
(74) *Attorney, Agent, or Firm* — Holtz Holtz Goodman & Chick PC

(57) ABSTRACT

An object of the present invention is to provide better formulations of a latanoprost ophthalmic solution. The present invention provides a clear ophthalmic solution comprising latanoprost as an active ingredient and benzalkonium chloride as a preservative wherein white turbidity due to a change of formulation is prevented by at least one means selected from the following 1) to 3); 1) adding a surfactant, 2) using benzalkonium chloride represented by the formula of $[C_6H_5CH_2N(CH_3)_2R]Cl$ (wherein R is alkyl having 12 carbon atoms) as the preservative and 3) adding a nonionic tonicity agent as a tonicity agent.

2 Claims, No Drawings

TRANSPARENT EYE DROPS CONTAINING LATANOPROST

This application is the United States national phase application of International Application PCT/JP2003/11402 filed Sep. 8, 2003.

TECHNICAL FIELD

The present invention relates to a clear and stable ophthalmic solution comprising latanoprost, which is useful as a therapeutic agent for glaucoma, as an active ingredient.

BACKGROUND ART

Latanoprost is a prostaglandin-type therapeutic agent for glaucoma represented by a chemical name of isopropyl (Z)-7[(1R,2R,3R,5S)3,5-dihydroxy-2-[(3R)-3-hydroxy-5-phenylpentyl]cyclopentyl]-5-heptanoate. Latanoprost is a selective FP receptor agonist and lowers intraocular pressure by promoting outflow of an aqueous humor (See, for example, Japanese Patent No. 2721414). An administration route of latanoprost is instillation, and an ophthalmic solution containing 0.005% latanoprost (trade name: Xalatan ophthalmic solution) is commercially available.

An object of the present invention is to provide better formulations of a latanoprost ophthalmic solution.

As a preservative of the ophthalmic solution, benzalkonium chloride (hereinafter abbreviated as "BAK") is the most widely used from the standpoint of effects and the like. However, while BAK has an excellent preservative effect, BAK may cause corneal disorders when it is used at a high concentration. Accordingly, when BAK is added to the ophthalmic solution, it is desirable to lower its concentration as low as possible.

BAK described in the specification means a mixture of compounds having a chemical structure represented by $[C_6H_5CH_2N(CH_3)_2R]Cl$ wherein alkyl (represented by R) is $C_8H_{17} \sim C_{18}H_{37}$.

BAK is defined as follows in Japanese, United States and European Pharmacopoeia.

Japanese Pharmacopoeia: BAK is represented by $[C_6H_5CH_2N(CH_3)_2R]Cl$ wherein R is $C_8H_{17} \sim C_{18}H_{37}$ and mainly comprises $C_{12}H_{25}$ and $C_{14}H_{29}$.

United States Pharmacopoeia: BAK is a mixture of alkylbenzyldimethylammonium chloride represented by $[C_6H_5CH_2N(CH_3)_2R]Cl$ wherein R is a mixture of all or some alkyl groups which are higher than $C_8H_{17}$ and mainly comprises $C_{12}H_{25}$, $C_{14}H_{29}$ and $C_{16}H_{33}$.

European Pharmacopoeia: BAK is a mixture of alkylbenzyldimethylammonium chloride wherein alkyl has chain length of $C_8$ to $C_{18}$.

On the other hand, a tonicity agent is usually added to the ophthalmic solution in order to keep isotonicity and is exemplified by inorganic salts such as alkali metal salts such as sodium chloride and alkaline earth metal salts such as magnesium chloride.

Further, a buffer is usually added to the ophthalmic solution in order to prevent a change of pH and is exemplified by inorganic salts such as sodium phosphate and sodium borate and organic salts such as sodium acetate, sodium citrate and sodium carbonate.

The tonicity agent and the buffer are contained in a commercially available latanoprost ophthalmic solution.

The present inventors prepared and studied latanoprost ophthalmic solutions containing these widely-used additives.

As a result, surprisingly it was turned out that white turbidity is not observed at a BAK concentration of 0.015% or higher, while it is observed at a BAK concentration of 0.01% or lower. That is because hydrophobic latanoprost and BAK form a complex, and the latanoprost-BAK complex is precipitated due to a salting-out effect by salts, i.e. additives. The present inventors discovered the fact, to their surprise, that the complex is not precipitated until the BAK concentration is lowered to 0.01% or lower. Since the commercially available latanoprost ophthalmic solution (trade name: Xalatan ophthalmic solution) contains 0.02% of BAK, a problem of white turbidity is not caused. However, as mentioned above, though BAK is the excellent preservative, it may cause the corneal disorders when used at the high concentration. Accordingly, when BAK is added to the ophthalmic solution, it is desirable to lower its concentration as low as possible.

DISCLOSURE OF THE INVENTION

First studying various additives for preventing white turbidity, the present inventors found that white turbidity can be prevented by adding a surfactant.

Carrying out intensive studies by focusing attention on the kind of BAK, it was found that white turbidity can be prevented not by using a mixture of compounds represented by the above chemical structural formula wherein alkyl has 8 to 18 carbon atoms but by using BAK in which alkyl has 12 carbon atoms.

Further, the present inventors considered that use of salts as tonicity agents may be a cause of white turbidity and carried out precise studies focusing attention on the kind of tonicity agent. As a result, it was found that white turbidity can be prevented by using nonionic tonicity agents as tonicity agents.

Namely, it was found that a clear ophthalmic solution comprising latanoprost as an active ingredient and benzalkonium chloride as a preservative, wherein white turbidity due to a change of formulation is prevented by at least one means selected from the following 1) to 3), is obtained;
1) adding a surfactant,
2) using benzalkonium chloride represented by the formula of $[C_6H_5CH_2N(CH_3)_2R]Cl$ (wherein R is alkyl having 12 carbon atoms) as the preservative and
3) adding a nonionic tonicity agent as a tonicity agent.

The above-mentioned three means can be used solely or in combination.

A concentration of latanoprost, which is the active ingredient of the ophthalmic solution in the present invention, is preferably 0.001 to 0.01% (W/V), particularly preferably 0.005% (W/V).

The first means in the present invention is adding a surfactant. When the surfactant is added, the clear latanoprost ophthalmic solution wherein white turbidity is prevented can be obtained independently of the kind of tonicity agent and the kind of BAK.

Examples of surfactants are Polysorbate 80, polyoxyethylene hydrogenated castor oil 60, polyoxyl 35 castor oil, polyethylene glycol monostearate, macrogol 4000, lecithin, sucrose ester, polyoxyethylene alkyl ether, polyoxyl stearate, polyoxyethylene polyoxypropylene glycol and the like, preferably Polysorbate 80, polyoxyethylene hydrogenated castor oil 60 and polyoxyl 35 castor oil. A concentration of the surfactant is preferably 0.001 to 0.5%.

The second means in the present invention is using benzalkonium chloride represented by the formula of $[C_6H_5CH_2N(CH_3)_2R]Cl$ (wherein R is alkyl having 12 carbon atoms) as a preservative. Benzalkonium chloride wherein alkyl has 12 carbon atoms described in the specification (hereinafter abbreviated as "BAK-$C_{12}$") means benzalkonium chloride which has a chemical structure represented by [$C_6H_5CH_2N(CH_3)_2R$]Cl and whose alkyl (represented by R in the formula) is $C_{12}H_{25}$.

The clear latanoprost ophthalmic solution wherein white turbidity is prevented can be obtained independently of the kind of tonicity agent by using BAK-$C_{12}$ as a preservative.

Commercially available BAK-$C_{12}$ can be used. A concentration of BAK-$C_{12}$ is preferably 0.01% (W/V) or lower. When the BAK concentration is too low, the sufficient preservative effect is not exhibited. Accordingly, a more preferred BAK concentration is in the range of 0.003 to 0.01% (W/V).

The third means in the present invention is adding a nonionic tonicity agent as a tonicity agent. The clear latanoprost ophthalmic solution wherein white turbidity is prevented can be obtained independently of the kind of BAK by using the nonionic tonicity agent. When the nonionic tonicity agent is used, a total amount of salts in the ophthalmic solution can be reduced. As a result, an influence of a salting-out effect is decreased, and thereby white turbidity is prevented.

The nonionic tonicity agents can be any agents to be usually used for ophthalmic solutions and are specifically exemplified by glycerin, mannitol, polyethylene glycol, propylene glycol, trehalose, sucrose and the like. A concentration of the nonionic tonicity agent is adjusted to a concentration which can be isotonic for each substance.

The ophthalmic solution of the present invention can be prepared optionally by adding a pH buffer, a pH adjusting agent, a solubilizer or a viscous agent. Examples of pH buffers are phosphates such as sodium phosphate, sodium dihydrogenphosphate, disodium hydrogenphosphate, potassium phosphate, potassium dihydrogenphosphate and dipotassium hydrogenphosphate; borates such as sodium borate and potassium borate; citrates such as sodium citrate and disodium citrate; acetates such as sodium acetate and potassium acetate; and carbonates such as sodium carbonate and sodium hydrogencarbonate. Examples of pH adjusting agents are hydrochloric acid, citric acid, phosphoric acid, acetic acid, sodium hydroxide, potassium hydroxide and the like. Examples of solubilizers are Polysorbate 80, polyoxyethylene hydrogenated castor oil 60, macrogol 4000 and the like. Examples of viscous agents are hydroxypropylmethylcellulose, hydroxypropylcellulose, polyvinyl alcohol, carboxyvinyl polymer, polyvinylpyrrolidone and the like.

A salt such as sodium chloride, potassium chloride calcium chloride or magnesium chloride can be added as the tonicity agent in the means 1 and 2.

pH of the ophthalmic solution of the present invention is preferably adjusted to 3 to 8, more preferably 4 to 7.

The ophthalmic solution of the present invention can be prepared by widely-used processes.

BEST MODE FOR CARRYING OUT THE INVENTION

Examples According to Means 1)

Example 1-1

Crystalline sodium dihydrogenphosphate (0.2 g), sodium chloride (0.8 g), Polysorbate 80 (0.01 g) and benzalkonium chloride (0.01 g) were dissolved in purified water (approximately 90 ml), pH was adjusted to 6.7, and purified water was added to the solution so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Example 1-2

Crystalline sodium dihydrogenphosphate (0.2 g), sodium chloride (0.8 g), polyoxyethylene hydrogenated castor oil 60 (0.01 g) and benzalkonium chloride (0.01 g) were dissolved in purified water (approximately 90 ml), pH was adjusted to 6.7, and purified water was added to the solution so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Example 1-3

Crystalline sodium dihydrogenphosphate (0.2 g), sodium chloride (0.8 g), polyoxyl 35 castor oil 60 (0.01 g) and benzalkonium chloride (0.01 g) were dissolved in purified water (approximately 90 ml), pH was adjusted to 6.7, and purified water was added to the solution so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Examples According to Means 2)

Example 2-1

Crystalline sodium dihydrogenphosphate (0.2 g), sodium chloride (0.8 g) and BAK-$C_{12}$ (0.01 g) were dissolved in purified water (approximately 90 ml), pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Example 2-2

Crystalline sodium dihydrogenphosphate (0.2 g), sodium chloride (0.8 g) and BAK-$C_{12}$ (0.005 g) were dissolved in purified water (approximately 90 ml), pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Examples According to Means 3)

Example 3-1

Crystalline sodium dihydrogenphosphate (0.2 g), concentrated glycerin (2.3 g) and BAK (0.01 g) were dissolved in purified water (approximately 90 ml), pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Example 3-2

Crystalline sodium dihydrogenphosphate (0.2 g), mannitol (4.5 g) and BAK (0.01 g) were dissolved in purified water (approximately 90 ml), pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Example 3-3

Crystalline sodium dihydrogenphosphate (0.2 g), polyethylene glycol 400 (8.0 g) and BAK (0.01 g) were dissolved in purified water (approximately 90 ml), pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Example 3-4

Crystalline sodium dihydrogenphosphate (0.2 g), propylene glycol (2.0 g) and BAK (0.01 g) were dissolved in purified water (approximately 90 ml), pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Example 3-5

Crystalline sodium dihydrogenphosphate (0.2 g), trehalose (9.0 g) and BAK (0.01 g) were dissolved in purified water (approximately 90 ml), pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7.

Experiment 1: Measurement of Residual Ratio of Latanoprost and Observation of Appearance 1) Comparative formulations 1 to 4 were prepared as follows.
Purified water (approximately 90 ml) was placed in a 100 ml-glass beaker. Crystalline sodium dihydrogenphosphate (0.2 g) and sodium chloride (0.9 g) were dissolved in the purified water, pH was adjusted to 6.7 with a 1 N aqueous sodium hydroxide solution, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7. Water for injection was added to the solution to adjust total volume to 100 ml. In a glass test tube was placed precisely 10 ml of the latanoprost solution, 50, 100, 150 or 200 μl of a 1% BAK (a mixture of compounds having 12, 14 and 16 carbon atoms of alkyl R in the above chemical structural formula) solution was added thereto, and they were mixed. These formulations are shown in Table 1.
2) Formulations 1 to 3 were prepared as follows.
Purified water (approximately 90 ml) was placed in a 100 ml-glass beaker. Crystalline sodium dihydrogenphosphate (0.2 g), sodium chloride (0.9 g) and each surfactant were dissolved in the purified water so that each concentration was the value shown in Table 2, pH was adjusted to 6.7 with an aqueous sodium hydroxide solution or diluted hydrochloric acid, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7. Water for injection was added to the solution to adjust total volume to 100 ml. In a glass test tube was placed precisely 10 ml of the latanoprost solution, 100 μl of a 1% BAK (a mixture of compounds having 12, 14 and 16 carbon atoms of alkyl R in the above chemical structural formula) solution was added thereto, and they were mixed. These formulations are shown in Table 2.
3) Formulations 4 and 5 were prepared as follows.
Purified water (approximately 90 ml) was placed in a 100 ml-glass beaker. Crystalline sodium dihydrogenphosphate (0.2 g) and sodium chloride (0.9 g) were dissolved in the purified water, pH was adjusted to 6.7 with a 1 N aqueous sodium hydroxide solution, and purified water was added to the mixture so that total volume was 10.0 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7. Water for injection was added to the solution to adjust total volume to 100 ml. In a glass test tube was placed precisely 10 ml of the latanoprost solution, 50 or 100 μl of a 1% BAK-$C_{12}$ solution was added thereto, and they were mixed. These formulations are shown in Table 3.
4) Formulations 6 to 10 were prepared as follows.
Purified water (approximately 90 ml) was placed in a 100 ml-glass beaker. Crystalline sodium dihydrogenphosphate (0.2 g) and each nonionic tonicity agent were dissolved in the purified water so that each concentration was the value shown in Table 4, pH was adjusted to 6.7 with an aqueous sodium hydroxide solution or diluted hydrochloric acid, and purified water was added to the mixture so that total volume was 100 ml to give a vehicle. The vehicle (100 ml) was added to latanoprost (5 mg), and the mixture was stirred while warming it in a water bath at about 80° C. to dissolve latanoprost in the vehicle. The temperature of the solution was returned to room temperature, and then pH was confirmed to be 6.7. Water for injection was added to the solution to adjust total volume to 100 ml. Into a glass test tube was placed precisely 10 ml of the latanoprost solution, 100 μl of a 1% BAK (a mixture of compounds having 12, 14 and 16 carbon atoms of alkyl R in the above chemical structural formula) solution was added thereto, and they were mixed. These formulations are shown in Table 4.

5) Appearance of each solution prepared by the above-mentioned method was observed, and precisely 1 ml of each solution was sampled in a 25-ml messflask. Nine milliliters of each remaining solution were filtered with a 0.2-µm filter.

6) Latanoprost concentrations in the solutions were measured before and after filtration by high performance liquid chromatography, and residual ratios were calculated.

TABLE 3

|  | Formulation 4 | Formulation 5 |
|---|---|---|
| Latanoprost | 0.005 | 0.005 |
| Crystalline sodium dihydrogenphosphate | 0.2 | 0.2 |
| Sodium chloride | 0.9 | 0.9 |
| BAK C-$_{12}$ | 0.01 | 0.005 |
| Diluted hydrochloric acid | q.s. | q.s. |
| Sodium hydroxide | q.s. | q.s. |
| Purified water | q.s. | q.s. |

(Unit in Table: % (W/V), q.s.: quantum sufficient)

TABLE 4

|  | Formulation 6 | Formulation 7 | Formulation 8 | Formulation 9 | Formulation 10 |
|---|---|---|---|---|---|
| Latanoprost | 0.005 | 0.005 | 0.005 | 0.005 | 0.005 |
| Crystalline sodium dihydrogenphosphate | 0.2 | 0.2 | 0.2 | 0.2 | 0.2 |
| BAK | 0.01 | 0.01 | 0.01 | 0.01 | 0.01 |
| Concentrated glycerin | 2.5 | — | — | — | 13 |
| Mannitol | — | 5 | — | — | — |
| PEG 400 | — | — | 8.5 | — | — |
| Propylene glycol | — | — | — | 2.1 | — |
| Trehalose | — | — | — | — | 9.25 |
| Diluted hydrochloric acid | q.s. | q.s. | q.s. | q.s. | q.s. |
| Sodium hydroxide | q.s. | q.s. | q.s. | q.s. | q.s. |
| Purified water | q.s. | q.s. | q.s. | q.s. | q.s. |

(Unit in Table: % (W/V), q.s.: quantum sufficient)

TABLE 1

|  | Comparative formulation 1 | Comparative formulation 2 | Comparative formulation 3 | Comparative formulation 4 |
|---|---|---|---|---|
| Latanoprost | 0.005 | 0.005 | 0.005 | 0.005 |
| Crystalline sodium dihydrogenphosphate | 0.2 | 0.2 | 0.2 | 0.2 |
| Sodium chloride | 0.9 | 0.9 | 0.9 | 0.9 |
| BAK | 0.02 | 0.015 | 0.01 | 0.005 |
| Diluted hydrochloric acid | q.s. | q.s. | q.s. | q.s. |
| Sodium hydroxide | q.s. | q.s. | q.s. | q.s. |
| Purified water | q.s. | q.s. | q.s. | q.s. |

(Unit in Table: % (W/V), q.s.: quantum sufficient)

TABLE 2

|  | Formulation 1 | Formulation 2 | Formulation 3 |
|---|---|---|---|
| Latanoprost | 0.005 | 0.005 | 0.005 |
| Crystalline sodium dihydrogenphosphate | 0.2 | 0.2 | 0.2 |
| Sodium chloride | 0.9 | 0.9 | 0.9 |
| BAK | 0.01 | 0.01 | 0.01 |
| Polysorbate 80 | 0.01 | — | — |
| Polyoxyethylene hydrogenated castor oil 60 | — | 0.01 | — |
| Polyoxyl 35 castor oil | — | — | 0.01 |
| Diluted hydrochloric acid | q.s. | q.s. | q.s. |
| Sodium hydroxide | q.s. | q.s. | q.s. |
| Purified water | q.s. | q.s. | q.s. |

(Unit in Table: % (W/V), q.s.: quantum sufficient)

Results

Table 5 shows results of appearance observation and residual ratio measurement of comparative formulations 1 to 4. In comparative formulations 1 and 2 containing 0.02% or 0.015% of BAK added to latanoprost, appearance was colorless and transparent, and residual ratios were 96.8 to 99.4%. That is to say, the formulations did not change. However, in comparative formulations 3 and 4 containing 0.01% or 0.005% of BAK, white turbidity was observed, and residual ratios decreased. That is to say, the formulations changed.

Table 6 shows results of appearance observation and residual ratio measurement of formulations 1 to 3 (means 1). In comparative formulations 3 and 4, white turbidity was observed, and the residual ratios decreased. To the contrary, in formulations 1 to 3 containing the surfactant, white turbidity was not observed, and residual ratios kept high values, i.e., 97.2 to 99.8%. These results show that when the surfactant is added to the formulations comprising latanoprost and BAK, the surfactant prevents the formulation from changing, and thereby stable and clear ophthalmic solutions are obtained.

Table 7 shows results of appearance observation and residual ratio measurement of formulations 4 and 5 (means 2). In comparative formulations 3 and 4 using BAK, white turbidity was observed, and the residual ratios decreased. To the contrary, in formulations 4 and 5 containing BAK-$C_{12}$ instead of BAK, white turbidity was not observed, and residual ratios were 97.3 to 98.2%. That is to say, the formulations did not change. These results show that when BAK-$C_{12}$ is added instead of BAK to the formulation comprising latanoprost, BAK-$C_{12}$ prevents the formulation from changing, and thereby stable and clear ophthalmic solutions are obtained.

Table 8 shows results of appearance observation and residual ratio measurement of formulations 6 to 10. In comparative formulations 3 and 4 containing sodium chloride as the tonicity agent, white turbidity was observed, and the residual ratios decreased. To the contrary, in formulations 6 to 10 containing the nonionic tonicity agent instead of sodium chloride, white turbidity was not observed, and residual ratios were 94.6 to 98.6%. That is to say, the formulations did not change. These results show that when the nonionic tonicity agent is added as a tonicity agent to the formulations comprising latanoprost and BAK, the agent prevents the formulation from changing, and thereby stable and clear ophthalmic solutions are obtained.

TABLE 5

|  | Comparative formulation 1 | Comparative formulation 2 | Comparative formulation 3 | Comparative formulation 4 |
|---|---|---|---|---|
| Appearance | Colorless and transparent | Colorless and transparent | White turbidity | White turbidity |
| Residual ratio (%) | 99.4 | 96.8 | 67.3 | 83.5 |

TABLE 6

|  | Formulation 1 | Formulation 2 | Formulation 3 |
|---|---|---|---|
| Appearance | Colorless and transparent | Colorless and transparent | Colorless and transparent |
| Residual ratio (%) | 99.8 | 98.0 | 97.2 |

TABLE 7

|  | Formulation 4 | Formulation 5 |
|---|---|---|
| Appearance | Colorless and transparent | Colorless and transparent |
| Residual ratio (%) | 97.3 | 98.2 |

TABLE 8

|  | Formulation 6 | Formulation 7 | Formulation 8 | Formulation 9 | Formulation 10 |
|---|---|---|---|---|---|
| Appearance | Colorless and transparent | Colorless and transparent | Colorless and transparent | Colorless and transparent | Colorless and transparent |
| Residual ratio (%) | 98.6 | 96.0 | 94.6 | 98.2 | 96.2 |

TABLE 9

|  | Microbe | number on innoculation | Microbe number after four weeks | | |
|---|---|---|---|---|---|
|  |  |  | Example 1-1 | Example 2-1 | Example 3-1 |
| Bacteria | E.coli | $1.4 \times 10^6$ | Not detected | Not detected | Not detected |
|  | P. areruginosa | $8.9 \times 10^6$ | Not detected | Not detected | Not detected |
|  | S.aureus | $2.2 \times 10^6$ | Not detected | Not detected | Not detected |
| Fungus | C.albicans | $8.2 \times 10^6$ | Not detected | Not detected | $1.1 \times 10^3$ |
|  | A.niger | $9.0 \times 10^6$ | Not detected | 10 or fewer | Not detected |

INDUSTRIAL APPLICABILITY

By adding a surfactant, clear latanoprost ophthalmic solutions can be provided even if a BAK concentration is lowered. In addition, by using BAK-$C_{12}$ as a preservative, clear latanoprost ophthalmic solutions can be provided even if the BAK concentration is lowered, too. Further, by adding a nonionic tonicity agent, clear latanoprost ophthalmic solutions can be also provided even if the BAK concentration is lowered.

The invention claimed is:

1. A clear ophthalmic solution comprising (i) latanoprost having a concentration of 0.005% (W/V), (ii) 0.003 to 0.01% (W/V) of benzalkonium chloride represented by the formula of $[C_6H_5CH_2N(CH_3)_2R]Cl$, wherein R is an alkyl group having 12 carbon atoms and (iii) at least one pharmaceutically acceptable carrier selected from the group consisting of crystalline sodium dihydrogenphosphate sodium chloride, diluted hydrochloric acid and sodium hydroxide.

2. A method of preventing white turbidity in an ophthalmic solution comprising latanoprost having a concentration of 0.005% (WV) and at least one pharmaceutically acceptable carrier selected from the group consisting of crystalline sodium dihydrogenphosphate, sodium chloride, diluted hydrochloric acid and sodium hydrogen, the method comprising adding to said solution 0.003 to 0.01% (W/V) benzalkonium chloride represented by the formula $[C_6H_5CH_2N(CH_3)_2R]Cl$, wherein R is an alkyl group having 12 carbon atoms.

Experiment 2: Antimicrobial Effectiveness Tests

Antimicrobial effectiveness tests were carried out for the above-mentioned Examples 1-1, 2-1 and 3-1, according to the antimicrobial effectiveness test method described in the 13th revised Japanese Pharmacopoeia.

Test results are shown in Table 9. In the case of bacteria, after four weeks from inoculation, the bacteria was not detected in any Examples. In the case of fungus, after four weeks from inoculation, the fungus was not detected or the number was remarkably fewer than that of inoculated fungus. Accordingly, the preservative effect was found to be sufficiently exhibited.

* * * * *